(12) United States Patent
Kim et al.

(10) Patent No.: US 10,857,154 B2
(45) Date of Patent: Dec. 8, 2020

(54) PHARMACEUTICAL COMPOSITION CONTAINING KERATIN 8 PHOSPHORYLATION INHIBITOR FOR PREVENTING OR TREATING MACULAR DEGENERATION, AND METHOD FOR SCREENING MACULAR DEGENERATION MEDICINE

(71) Applicant: KONKUK UNIVERSITY INDUSTRIAL COOPERATION CORP, Seoul (KR)

(72) Inventors: Dong-Eun Kim, Seoul (KR); Ah Ruem Baek, Daejeon (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 0 days.

(21) Appl. No.: 16/302,934

(22) PCT Filed: May 18, 2017

(86) PCT No.: PCT/KR2017/005189
§ 371 (c)(1),
(2) Date: Nov. 19, 2018

(87) PCT Pub. No.: WO2017/200325
PCT Pub. Date: Nov. 23, 2017

(65) Prior Publication Data
US 2019/0275044 A1 Sep. 12, 2019

(30) Foreign Application Priority Data
May 19, 2016 (KR) .................. 10-2016-0061259

(51) Int. Cl.
| | | |
|---|---|---|
| *A61K 31/519* | (2006.01) | |
| *A61P 27/02* | (2006.01) | |
| *A61K 31/5377* | (2006.01) | |
| *A61K 31/4184* | (2006.01) | |
| *A61K 31/517* | (2006.01) | |
| *G01N 33/533* | (2006.01) | |
| *G01N 33/50* | (2006.01) | |
| *G01N 33/53* | (2006.01) | |

(52) U.S. Cl.
CPC ........ *A61K 31/519* (2013.01); *A61K 31/4184* (2013.01); *A61K 31/517* (2013.01); *A61K 31/5377* (2013.01); *A61P 27/02* (2018.01); *G01N 33/50* (2013.01); *G01N 33/53* (2013.01); *G01N 33/533* (2013.01)

(58) Field of Classification Search
CPC .......... A61K 31/519; A61K 31/517; A61K 31/4184; A61K 31/5377; A61P 27/02
See application file for complete search history.

(56) References Cited

U.S. PATENT DOCUMENTS

| | | | | |
|---|---|---|---|---|
| 5,770,599 | A * | 6/1998 | Gibson | C07D 403/12 514/228.2 |
| 7,378,423 | B2 * | 5/2008 | Kawasaki | C07D 471/04 514/264.1 |
| 8,835,443 | B2 * | 9/2014 | Kawasaki | C07D 471/04 514/262.1 |
| 9,725,447 | B2 * | 8/2017 | Springer | C07D 471/04 |
| 9,750,761 | B2 * | 9/2017 | Kottmann | A61K 31/713 |
| 10,004,803 | B2 * | 6/2018 | Mannick | G01N 33/6854 |

FOREIGN PATENT DOCUMENTS

| | | |
|---|---|---|
| KR | 10-0511720 B1 | 9/2005 |
| KR | 10-2010-0004466 A | 1/2010 |
| KR | 10-1244711 B1 | 3/2013 |
| KR | 10-1388635 B1 | 4/2014 |
| KR | 10-1414922 B1 | 7/2014 |
| KR | 10-1415221 B1 | 7/2014 |
| KR | 10-2014-0113912 A | 9/2014 |
| KR | 10-1483581 B1 | 1/2015 |
| KR | 10-1558498 B1 | 10/2015 |
| KR | 10-2015-0134796 A | 12/2015 |
| WO | 2012/118632 A1 | 9/2012 |

OTHER PUBLICATIONS

Hunt et al., "Altered Expression of Keratin and Vimentin in Human Retinal Pigment Epithelial Cells In Vivo and In Vitro", 1990, Journal of Cellular Physiology, 145(2), pp. 187-199. (Year: 1990).*
Lopez et al., "Transclifferentiated Retinal Pigment Epithelial Cells Are Immunoreactive for Vascular Endothelial Growth Factor in Surgically Excised Age-Related Macular Degeneration Related Choroidal Neovascular Membranes", 1996, Investigative Ophthalmology&: Visual Science, 37(5), pp. 855-868. (Year: 1996).*
Ku et al., "Keratin 8 Phosphorylation by p38 Kinase Regulates Cellular Keratin Filament Reorganization", 2002, J. Biol. Chem., 277(3), pp. 10775-10782. (Year: 2002).*
Tullo et al., "Ocular findings in patients with solid tumours treated with the epidermal growth factor receptor tyrosine kinase inhibitor gefitinib ('Iressa', ZD1839) in Phase I and II clinical trials", 2005, Eye, 19(5), pp. 729-738. (Year: 2005).*

(Continued)

*Primary Examiner* — My-Chau T. Tran
(74) *Attorney, Agent, or Firm* — Servilla Whitney LLC

(57) ABSTRACT

The present invention relates to a pharmaceutical composition for preventing or treating macular degeneration containing trametinib or gefitinib, and to a method of screening a therapeutic agent for macular degeneration. The pharmaceutical composition of the present invention is capable of inhibiting the phosphorylation of keratin 8 and the reorganization thereof around nuclei in retinal pigment epithelial cells under oxidative stress conditions, increasing the expression of E-cadherin, and reducing the expression of vimentin, and can thus be efficiently useful for the prevention or treatment of macular degeneration.

5 Claims, 10 Drawing Sheets

(56) References Cited

OTHER PUBLICATIONS

Chung et al., "Cytoskeletal Keratin Phosphorylation Induced by Autophagy Protects Retinal Pigment Epithelial Cells from Apoptosis during Oxidative Stress", 2012, Invest. Ophthalmol. Vis. Sci., ARVO Annual Meeting Abstract; 53(14):4751. (Year: 2012).*
Duncan et al., "MEK inhibitors: a new class of chemotherapeutic agents with ocular toxicity", 2015, Eye, 29(8), pp. 1003-1012. (Year: 2015).*
Kyosseva, Svetlana V., "Targeting MAPK Signaling in Age-Related Macular Degeneration", Jan. 2016, Ophthalmology and Eye Diseases, vol. 8, pp. 23-30. (Year: 2016).*
Baek et al., "Autophagy and KRT8/keratin 8 protect degeneration of retinal pigment epithelium under oxidative stress", 2017, Autophagy, 13(2), pp. 248-263. (Year: 2017).*
Gonzalez-Cao et al., "Other targeted drugs in melanoma", Ann Transl Med, vol. 3, No. 18, p. 266 (17 pages), (2015).

* cited by examiner

[Fig. 1]
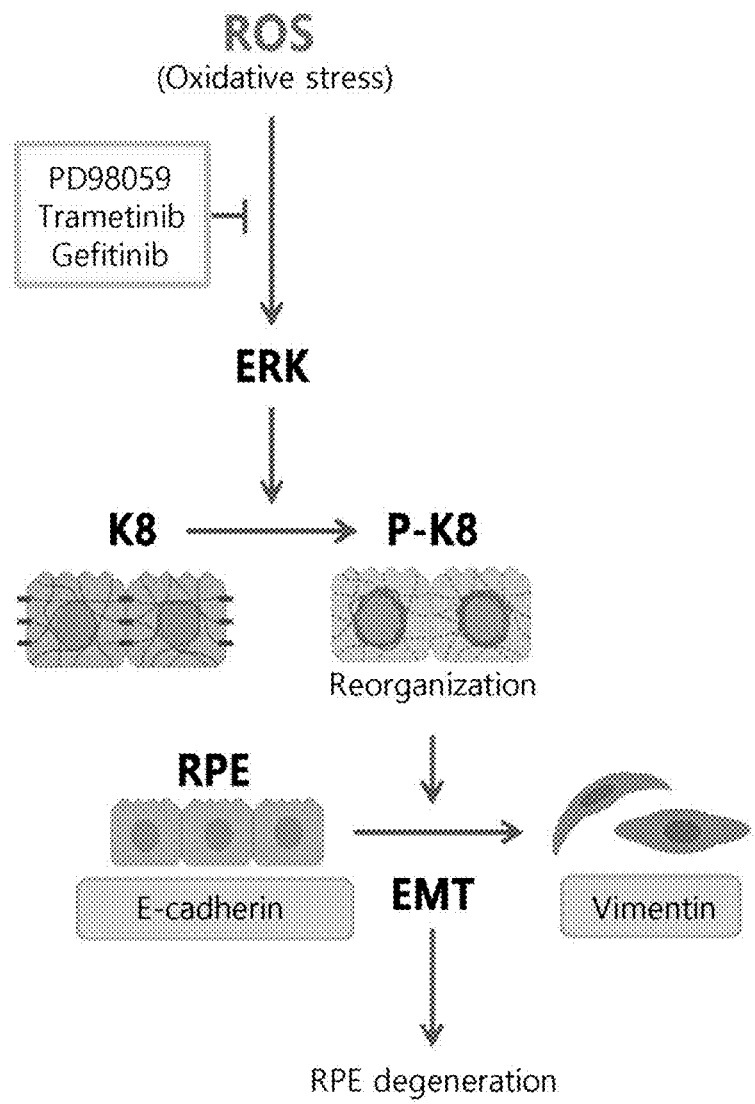

[Fig. 2A]
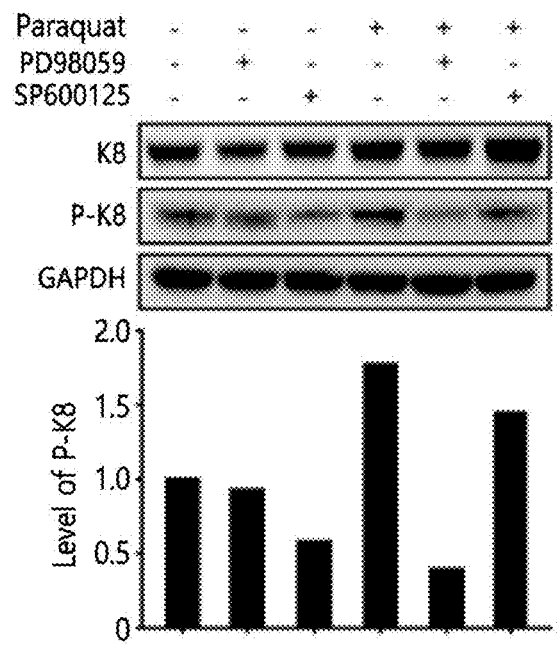
[Fig. 2B]
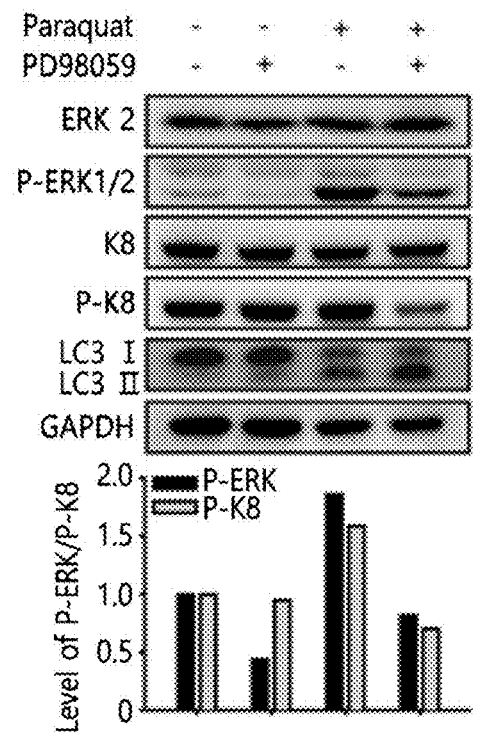

[Fig. 2C]
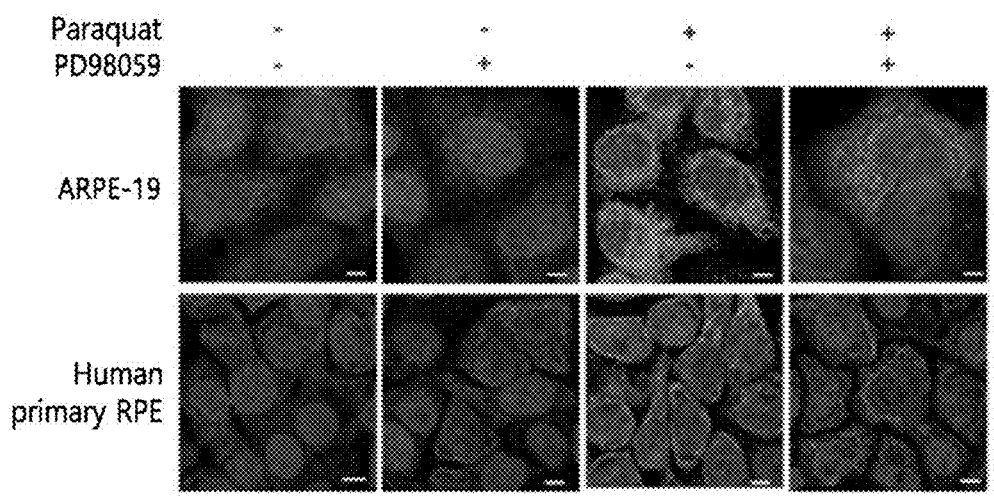

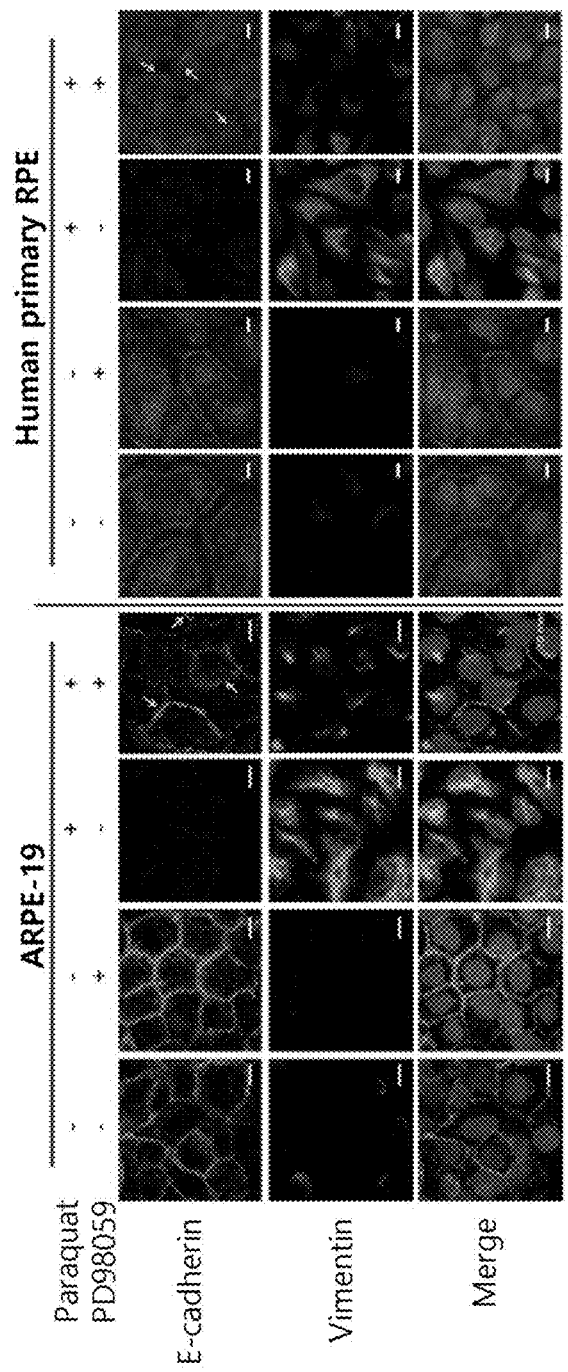
[Fig. 3A]

[Fig. 3B]
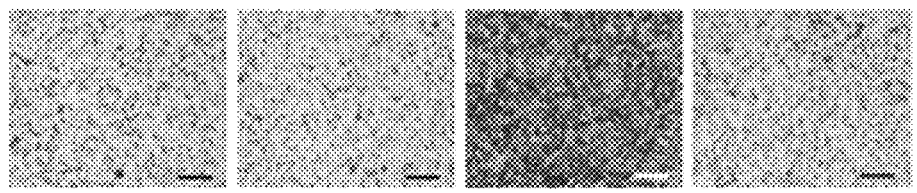
[Fig. 3C]

[Figure 4A]
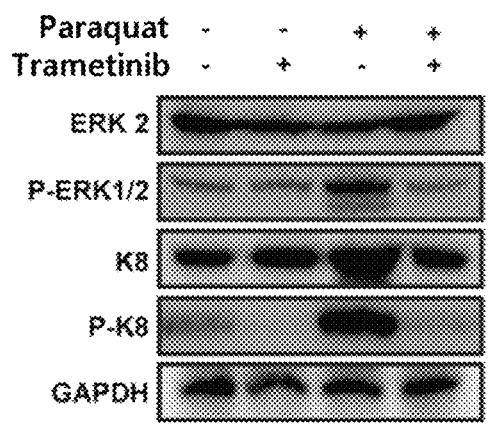
[Figure 4B]
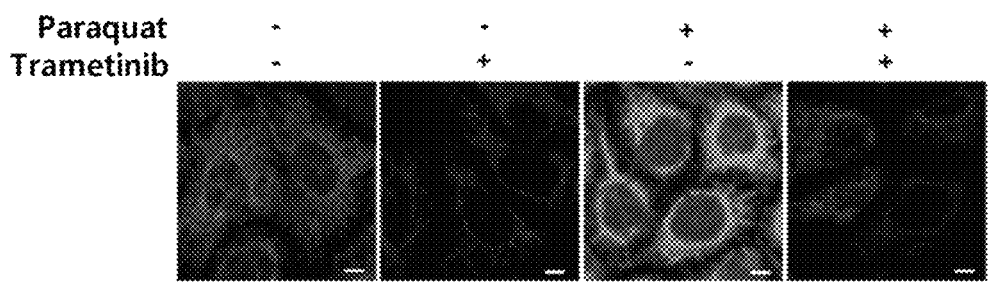

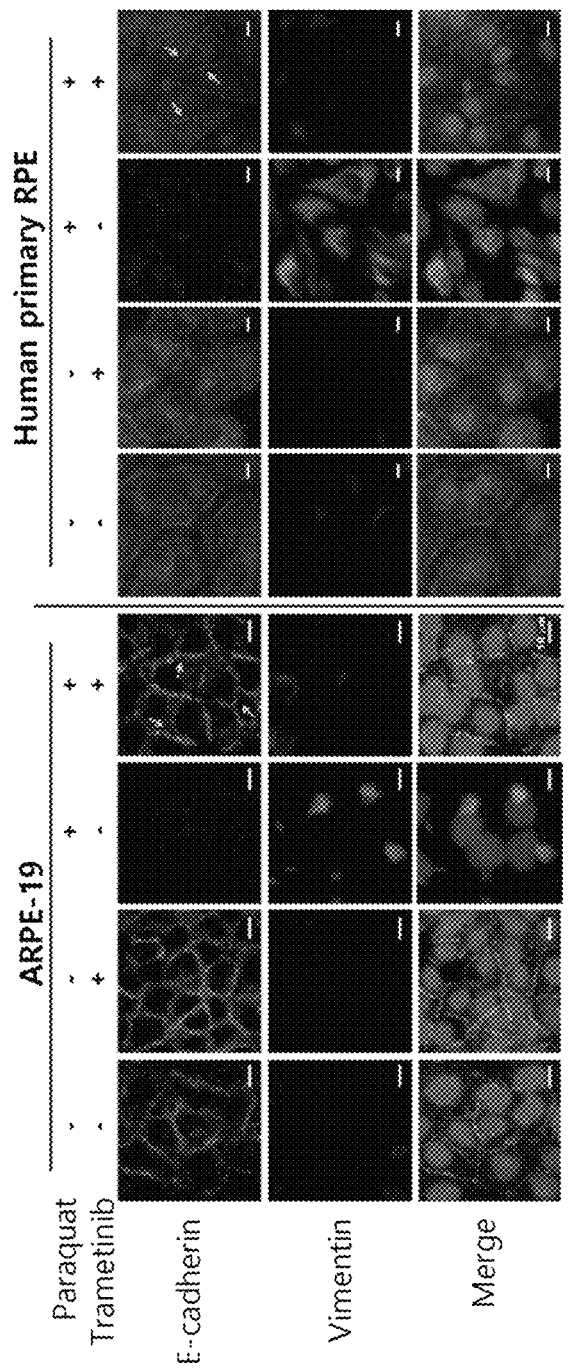

[Fig. 5A]
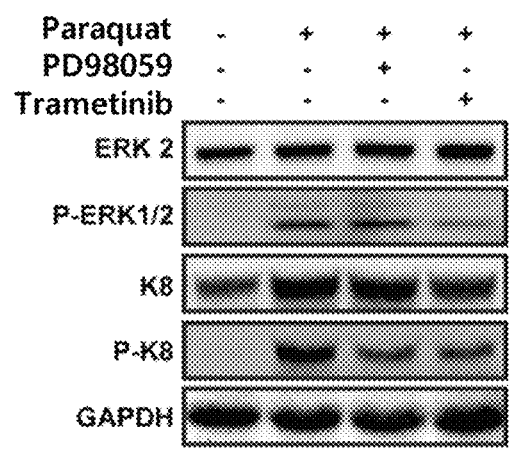
[Fig. 5B]
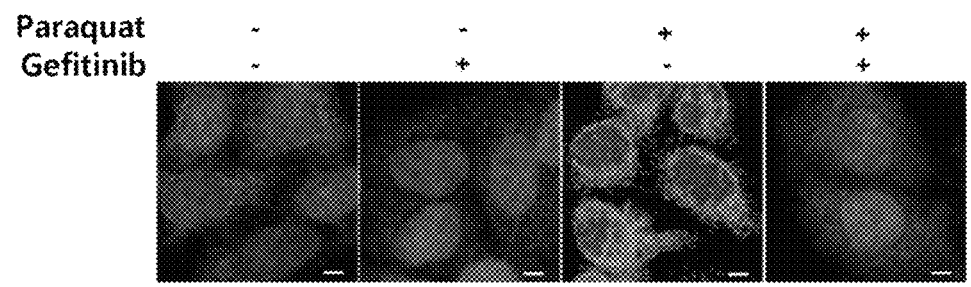

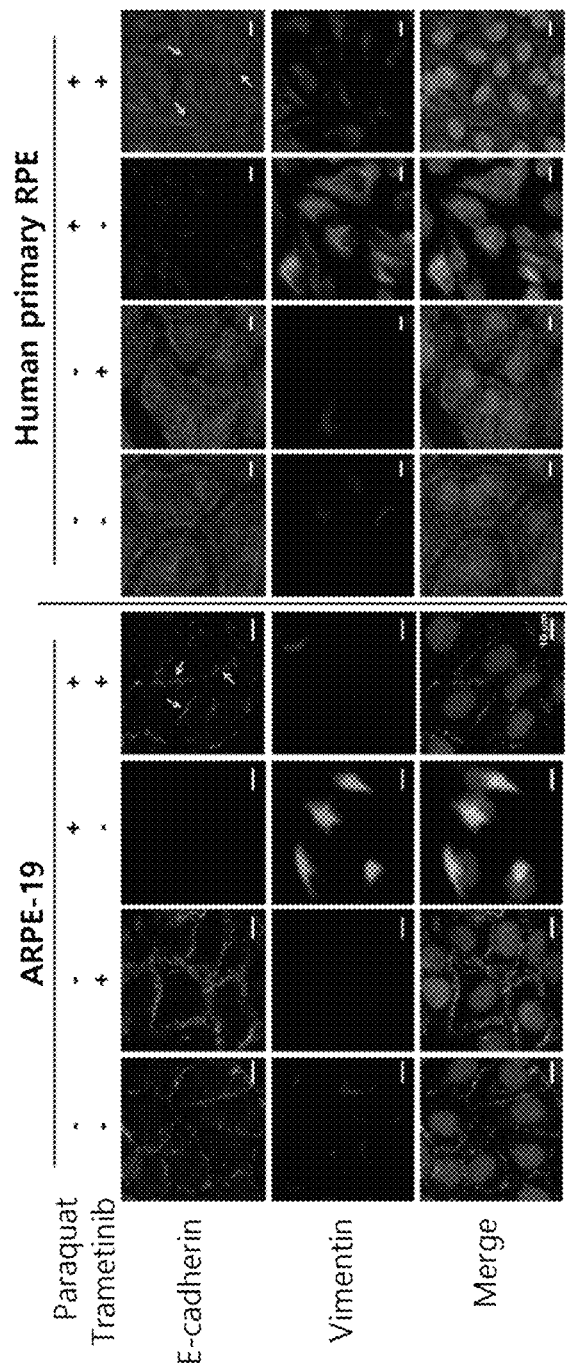
[Fig. 5C]

[Fig. 6]
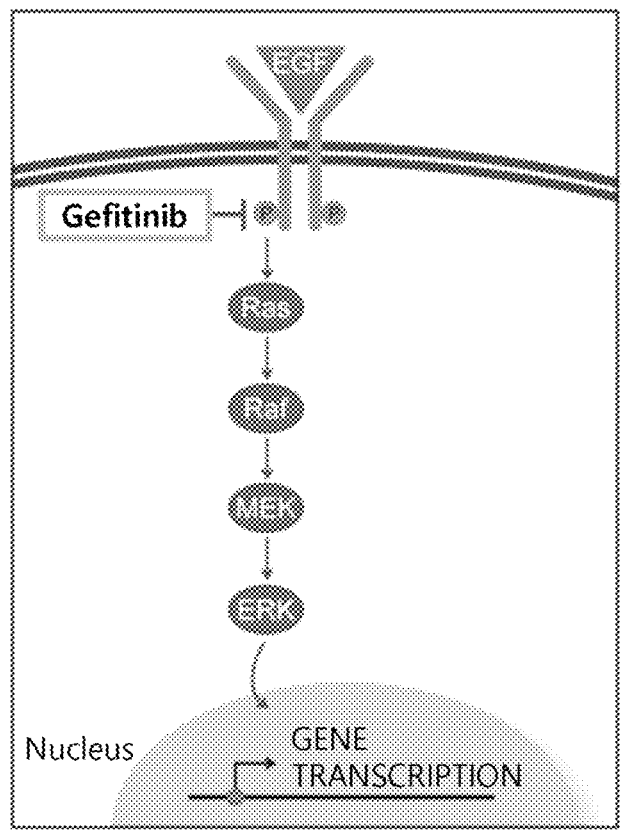

PHARMACEUTICAL COMPOSITION CONTAINING KERATIN 8 PHOSPHORYLATION INHIBITOR FOR PREVENTING OR TREATING MACULAR DEGENERATION, AND METHOD FOR SCREENING MACULAR DEGENERATION MEDICINE

TECHNICAL FIELD

The present invention relates to a pharmaceutical composition for the prevention or treatment of macular degeneration containing a keratin 8 phosphorylation inhibitor and to a method of screening a therapeutic agent for macular degeneration. More particularly, the present invention relates to a pharmaceutical composition for the prevention or treatment of dry macular degeneration, comprising trametinib or gefitinib, and to a method of screening a therapeutic agent for dry macular degeneration for inhibiting phosphorylation of keratin 8.

BACKGROUND ART

Macular degeneration, in which the central part of the visual field is blurred or distorted as the macular part existing in the retina degenerates with age, is classified into dry macular degeneration, resulting from accumulation of drusen, the cell metabolite remnant, between the retinal layer and the basement membrane thereunder, and wet macular degeneration, resulting from the growth of abnormal blood vessels and thus blood leakage. Wet macular degeneration arises from promoting angiogenesis by a growth factor such as a vascular endothelial growth factor (VEGF), and direct causes thereof have been identified, and various drugs (Avastin, Lucentis, Eylea) targeting the same have been developed. However, dry macular degeneration, which accounts for approximately 90% of patients, has not been studied much, and drugs therefor have not yet been developed. Although dry macular degeneration is known to have no significant effect on visual acuity, the development of a therapeutic agent for dry macular degeneration is urgent because dry macular degeneration is known to progress into wet macular degeneration.

The inventors of the present invention have investigated that when extracellular signal-regulated kinase (ERK) is activated due to oxidative stress, which is a main cause of macular degeneration, keratin 8 (K8), which plays a role in the intracellular skeleton, is phosphorylated, and K8, which is widely distributed throughout the cytoplasm in normal cells, is phosphorylated by ERK in the cells exposed to oxidative stress and thus reorganized around the nucleus of the cells. The reorganization of phosphorylated K8 around the nucleus increases cell motility, and cells that have undergone this process lose the properties of epithelial cells and enter a state of epithelial-mesenchymal transition (EMT).

When retinal epithelial cells lose their properties and acquire the properties of mesenchymal cells, having high cell motility, the dense retinal layer is disturbed. This phenomenon is responsible for geographic atrophy (GA), which is a later stage of dry macular degeneration. GA patients are at high risk for developing choroidal neovascularization (CNV), and when the CNV is released by stress and small impacts, the blood leaks, resulting in wet macular degeneration. Therefore, it is very important to prevent EMT of the retinal epithelial cells in order to inhibit the progression of dry macular degeneration and conversion into wet macular degeneration.

With regard thereto, Korean Patent No. 10-1415221 (Jun. 27, 2014) discloses a pharmaceutical composition for the prevention and treatment of angiogenesis-related disease containing, as an active ingredient, inorganic nanoparticles selected from among silica and titanium oxide, the angiogenesis-related disease including macular degeneration.

DISCLOSURE

Technical Problem

Accordingly, the inventors of the present invention have studied the treatment of macular degeneration and have ascertained that trametinib or gefitinib is capable of inhibiting the phosphorylation of keratin 8 and is thus useful in the prevention or treatment of macular degeneration.

Accordingly, the present invention is intended to provide a pharmaceutical composition for the prevention or treatment of macular degeneration comprising trametinib or gefitinib, and a method of screening a therapeutic agent for macular degeneration.

Technical Solution

An aspect of the present invention provides a pharmaceutical composition for preventing or treating macular degeneration, comprising one or more keratin 8 (K8) phosphorylation inhibitor selected from the group consisting of trametinib, gefitinib, canertinib, lapatinib, erlotinib, afatinib, neratinib, selumetinib, refametinib, and PD98059.

In an embodiment, the keratin 8 phosphorylation inhibitor may be trametinib or gefitinib.

In an embodiment, the macular degeneration may be dry macular degeneration, particularly dry macular degeneration caused by epithelial-mesenchymal transition.

In an embodiment, the pharmaceutical composition may further comprise a pharmaceutically acceptable diluent or carrier.

Another aspect of the present invention provides a method of screening a therapeutic agent for macular degeneration comprising selecting a candidate substance for inhibiting keratin 8 phosphorylation.

In an embodiment, the selecting the candidate substance may comprise: a) treating retinal pigment epithelial cells, in which keratin 8 is phosphorylated due to oxidative stress, with a candidate substance; b) determining whether or not keratin 8 phosphorylation is inhibited after treatment with the candidate substance; and c) determining the candidate substance to be effective for treatment of macular degeneration when keratin 8 phosphorylation is inhibited in a candidate-substance-treated group compared to a non-treated group.

In step b), when the expression level of P-ERK1/2 or P-K8 is reduced after treatment with the candidate substance, phosphorylation of keratin 8 may be determined to be inhibited.

In step b), when the expression level of E-cadherin is increased after treatment with the candidate substance, phosphorylation of keratin 8 may be determined to be inhibited.

In step b), when the expression level of vimentin is decreased after treatment with the candidate substance, phosphorylation of keratin 8 may be determined to be inhibited.

Advantageous Effects

According to the present invention, trametinib or gefitinib is found to inhibit phosphorylation of keratin 8 and reorganization thereof around the nucleus, to increase the expression of E-cadherin and to decrease the expression of vimentin. Therefore, trametinib or gefitinib according to the present invention can be efficiently used for the prevention or treatment of macular degeneration.

DESCRIPTION OF DRAWINGS

FIG. 1 schematically shows the degeneration of retinal epithelial cells due to oxidative stress;

FIGS. 2A and 2B shows the results of western blotting showing inhibition of ERK and K8 phosphorylation due to oxidative stress and FIG. 2C the results of cell staining showing inhibition of reorganization of K8 protein around the nucleus (scale bar: 5 µm), when using PD98059;

FIGS. 3A, 3B and 3C shows the results of cell staining showing (3A) inhibition of epithelial-mesenchymal transition of retinal epithelial cells (scale bar: 10 µm), (3B) inhibition of cell motility (scale bar: 0.5 mm) and (3C) cell protection activity through retinal degeneration inhibition in mouse model (scale bar: 50 µm), when using PD98059;

FIGS. 4A, 4B and 4C shows the results of (4A) western blotting showing inhibition of ERK and K8 phosphorylation in retinal epithelial cells due to oxidative stress and (4B) cell staining showing inhibition of reorganization of K8 around the nucleus (scale bar: 5 µm) and (4C) cell staining showing inhibition of epithelial-mesenchymal transition (scale bar: 10 µm), when using trametinib, an anticancer agent for inhibiting ERK phosphorylation;

FIGS. 5A, 5B and 5C shows the results of (5A) western blotting showing inhibition of ERK and K8 phosphorylation in retinal epithelial cells due to oxidative stress and (5B) cell staining showing inhibition of reorganization of K8 around the nucleus (scale bar: 5 µm) and (5C) cell staining showing inhibition of epithelial-mesenchymal transition (scale bar: 10 µm), when using gefitinib, an anticancer agent for inhibiting EGFR; and FIG. 6 schematically shows the signal transduction of an epithelial growth factor receptor and the EGFR phosphorylation inhibition of gefitinib.

BEST MODE

An aspect of the present invention pertains to a pharmaceutical composition for preventing or treating macular degeneration, comprising one or more keratin 8 (K8) phosphorylation inhibitor selected from the group consisting of trametinib, gefitinib, canertinib, lapatinib, erlotinib, afatinib, neratinib, selumetinib, refametinib, and PD98059.

Also, the present invention pertains to a keratin 8 phosphorylation inhibitor for use in the prevention or treatment of macular degeneration or to the use of a pharmaceutical composition comprising the same.

Also, the present invention pertains to a method of preventing or treating macular degeneration, comprising administering a patient with a keratin 8 phosphorylation inhibitor in a therapeutically effective amount.

In an embodiment, the keratin 8 phosphorylation inhibitor may be trametinib or gefitinib.

In an embodiment, the macular degeneration may be dry macular degeneration, particularly dry macular degeneration caused by epithelial-mesenchymal transition.

In an embodiment, the pharmaceutical composition may further comprising one or more pharmaceutically acceptable carrier or additive. Specifically, the pharmaceutical composition of the present invention may be formulated as oral dosage forms, such as powder, granule, tablet, capsule, suspension, emulsion, syrup, and aerosol formulations, as well as formulations for external use, suppositories, eye drops and sterile injectable solutions, in accordance with typical individual processes. The pharmaceutically acceptable carrier may include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil, and may also include excipients or diluents such as fillers, extenders, binders, wetting agents, disintegrants, surfactants, and the like. An oral solid formulation may include tablets, pills, powders, granules, capsules, and the like, and such a solid formulation may include one or more excipient, for example, starch, calcium carbonate, sucrose, lactose, gelatin, and the like, and may also include lubricants such as magnesium stearate, talc, etc. An oral liquid formulation may include suspensions, solutions, emulsions, or syrups, and may also include diluents, such as water or liquid paraffin, wetting agents, sweeteners, fragrances, and preservatives. A parenteral formulation may include sterilized aqueous solutions, non-aqueous solvents, suspensions, emulsions, freeze-dried preparations and suppositories. As non-aqueous solvents or suspensions, propylene glycol, polyethylene glycol, vegetable oil such as olive oil, injectable esters such as ethyl oleate, and the like may be used. As the base of the suppositories, Witepsol, Macrogol, Tween, cacao butter, laurin fat, glycerogelatin and the like may be used.

The dosage amount of the keratin 8 phosphorylation inhibitor comprised in the pharmaceutical composition of the present invention, when administered, may vary depending on the conditions and body weights of patients, the severity of disease, the drug form, and the administration route and time, and may be appropriately chosen by those skilled in the art. For example, the keratin 8 phosphorylation inhibitor may be administered in an amount of 0.0001 to 1000 mg/kg/day, and preferably 0.01 to 1000 mg/kg/day, and it may be administered once a day or several times a day. Also, the pharmaceutical composition of the present invention may comprise 0.001 to 90 wt % of the keratin 8 phosphorylation inhibitor based on the total weight of the composition.

The pharmaceutical composition of the present invention may be administered to mammals such as rats, mice, livestock, humans, and the like, through various routes, for example, oral, intraperitoneal, intrarectal, intravenous, intramuscular, subcutaneous, intrauterine epidural or intracerebroventricular injections.

Another aspect of the present invention pertains to a method of screening a therapeutic agent for macular degeneration, comprising selecting a candidate substance for inhibiting keratin 8 phosphorylation.

In an embodiment, the selecting the candidate substance may comprise a) treating retinal pigment epithelial cells, in which keratin 8 is phosphorylated due to oxidative stress, with a candidate substance; b) determining whether or not keratin 8 phosphorylation is inhibited after treatment with the candidate substance; and c) determining the candidate substance to be effective for the treatment of macular degeneration when keratin 8 phosphorylation is inhibited in a candidate-substance-treated group compared to a non-treated group.

In step b), when the expression level of P-ERK1/2 (phosphorylated ERK) or P-K8 (phosphorylated K8) is reduced after treatment with the candidate substance, phosphorylation of keratin 8 may be determined to be inhibited. The expression level P-ERK1/2 or P-K8 may be determined through western blotting assay.

In step b), when the expression level of E-cadherin is increased after treatment with the candidate substance, phosphorylation of keratin 8 may be determined to be inhibited. The expressed level of E-cadherin may be determined through immunofluorescence staining.

In step b), when the expression level of vimentin is decreased after treatment with the candidate substance, phosphorylation of keratin 8 may be determined to be inhibited. The expressed level of vimentin may be determined through immunofluorescence staining.

While K8 is phosphorylated in oxidative stress-induced retinal pigment epithelial cells, the expression level of E-cadherin is reduced and the expression level of vimentin is increased, whereby epithelial-mesenchymal transition (EMT) may progress. The term "epithelial-mesenchymal transition" refers to a process by which cells lose their epithelial phenotype and cell-cell adhesion and transform into high mobility state as a mesenchymal phenotype (FIG. 1).

A better understanding of the present invention will be given through the following examples, which are merely set forth to illustrate the present invention, but are not to be construed as limiting the scope of the present invention.

Examples

1. Inhibitory Effects of PD98059 on K8 Phosphorylation and Reorganization Thereof Around Nuclei Human retinal tissue-derived cells, APRE-19 cells (retinal pigment epithelial cells, American Type Culture Collection; CRL-2302) were selectively treated with 400 μM paraquat for 24 hr, and then treated with 10 μM SP600125 (JNK inhibitor) or 20 μM PD98059 (ERK inhibitor) for 24 hr. The expression level of P-K8 is exhibited in a bar graph resulting from western blotting (FIG. 2A). Based on these results, the effect of inhibiting K8 phosphorylation due to oxidative stress was confirmed to be superior when using PD98059 compared to using SP600125.

APRE-19 cells were treated with 400 μM paraquat for 24 hr, and then selectively treated with 20 μM PD98059 for 24 hr. The expression levels of ERK 2, P-ERK1/2 (phosphorylated ERK), K8, P-K8 and LC3 I/II were shown in a bar graph resulting from western blotting. In the bar graph analyzed from the image of western blotting, the expression levels of P-ERK and P-K8 were calculated (FIG. 2B). Based on these results, it was found that PD98059 inhibited K8 phosphorylation due to oxidative stress and that PD98059 was not involved in the expression of LC3 I/II, the autophagy marker.

APRE-19 cells and human-tissue-derived RPE cells (LONZA; 194987) were selectively treated with 400 μM paraquat and 20 μM PD98059 for 36 hr. The ARPE-19 cells are cell lines that have been genetically engineered for infinite proliferation for experimental use. However, as the human-tissue-derived RPE cells were obtained by culturing RPE tissue isolated from the human eye without any genetic engineering they were used for experiments under conditions similar to those of human RPE.

Thereafter, P-K8 (green fluorescence) of the cells was immunostained (Abcam; ab32579). The nucleus was stained (Invitrogen; T3605) using TOPRO-3 (blue fluorescence) (FIG. 2C). Consequently, it was found that PD98059 inhibited reorganization of K8 around the nucleus, represented as green, under oxidative stress conditions of the retinal epithelial cells induced by paraquat.

2. Inhibitory Effects of PD98059 on Epithelial-Mesenchymal Transition, Cell Motility and Retinal Degeneration APRE-19 cells and human-tissue-derived RPE cells were selectively treated with 400 μM paraquat and 20 μM PD98059 for 48 hr. E-cadherin (green fluorescence) and vimentin (red fluorescence) in the cells were immunostained (cell signaling; 7832s). The nucleus was stained using TOPRO-3 (blue fluorescence) (FIG. 3A). Consequently, it was found that PD98059 recovered E-cadherin lost, which is a consequence of epithelial-mesenchymal transition, and also inhibited an increase in vimentin filaments specifically shown in mesenchymal cells, under oxidative stress conditions of the retinal epithelial cells induced by paraquat. Therefore, PD98059 can be concluded to reduce epithelial-mesenchymal transition.

Also, the cell motility was analyzed using a Transwell insert in ARPE-19 cells selectively treated with 400 μM paraquat and 20 μM PD98059 for 36 hr. As the migrated cells were stained with methylene blue it was confirmed by checking an image (FIG. 3B). Consequently, it was found that PD98059 reduced increased cell motility under oxidative stress conditions of the retinal epithelial cells induced by paraquat.

7- to 9-week-old mouse retinal cells were subjected to immunohistochemical analysis (Abcam; ab59720) for a tight junction marker ZO-1 (green fluorescence). A saline-treated group was a control group with intravenous administration of 0.9% NaCl. A mouse group administered intravenously with 20 mg/kg of $NaIO_3$ was selectively treated with 10 mg/kg of PD98059. Animal groups were sacrificed 2 weeks after intravenous administration. The fluorescence images were obtained through a confocal microscope (FIG. 3C). Consequently, it was found that PD98059 restored the degeneration of retinal cells induced by $NaIO_3$.

3. Inhibitory Effect of Trametinib on Epithelial-Mesenchymal Transition

APRE-19 cells were selectively treated with 400 μM paraquat and 50 nM trametinib for 24 hr. The expression levels of ERK 2, P-ERK1/2 (phosphorylated ERK), K8, P-K8 and LC3 I/II were shown in a bar graph resulting from western blotting. In the bar graph analyzed from the image of western blotting, the expression levels of P-ERK and P-K8 were calculated (FIG. 4A). Consequently, it was found that trametinib inhibited K8 phosphorylation due to oxidative stress.

APRE-19 cells were selectively treated with 400 μM paraquat and 50 nM trametinib for 36 hr. P-K8 (green fluorescence) of the cells was immunostained (FIG. 4B). Consequently, it was found that trametinib inhibited reorganization of K8 around the nucleus, represented as green, under oxidative stress conditions of the retinal epithelial cells induced by paraquat.

APRE-19 cells and human-tissue-derived RPE cells were selectively treated with 400 μM paraquat and 50 nM trametinib for 48 hr. Thereafter, E-cadherin (green fluorescence) and vimentin (red fluorescence) in the cells were immunostained. The nucleus was visualized using TOPRO-3 (blue fluorescence) (FIG. 4C). Consequently, it was found that trametinib recovered E-cadherin lost and inhibited an increase in vimentin filaments under oxidative stress conditions of the retinal epithelial cells induced by paraquat. Therefore, trametinib can be concluded to reduce epithelial-mesenchymal transition.

4. Inhibitory Effect of Gefitinib on Epithelial-Mesenchymal Transition

The same procedures as in Example 3 were performed, and 10 µM gefitinib was used in lieu of 50 nM trametinib.

The expression levels of P-ERK and P-K8 were confirmed in a bar graph analyzed from the image western blotting. As shown in FIG. 5A, it was found that gefitinib inhibited phosphorylation of K8 due to oxidative stress.

As shown in FIG. 5B, it was found that gefitinib inhibited reorganization of K8 around the nucleus, represented as green, under oxidative stress conditions of the retinal epithelial cells induced by paraquat.

As shown in FIG. 5C, it was found that gefitinib recovered E-cadherin lost and inhibited the increase in vimentin filaments under oxidative stress conditions of the retinal epithelial cells induced by paraquat. Therefore, gefitinib can be concluded to reduce epithelial-mesenchymal transition.

EGFR (Epidermal Growth Factor Receptor), which is a receptor in the cell membrane, is known to be auto-phosphorylated to thus promote various intracellular signal transductions upon binding of ligands such as epidermal growth factor (EGF). Since ERK is one of the subfactors of EGFR, gefitinib is also deemed to inhibit the degeneration of retinal epithelial cells due to oxidative stress to thus be sufficiently useful as a therapeutic agent for macular degeneration (FIG. 6).

The invention claimed is:

1. A method of treating macular degeneration, the method comprising administering to a patient in need thereof a pharmaceutical composition comprising an effective amount of one or more keratin 8 (K8) phosphorylation inhibitor selected from the group consisting of trametinib, gefitinib, canertinib, lapatinib, erlotinib, afatinib, neratinib, selumetinib, refametinib, and PD98059.

2. The method of claim 1, wherein the keratin 8 phosphorylation inhibitor is trametinib or gefitinib.

3. The method of claim 1, wherein the macular degeneration is dry macular degeneration.

4. The method of claim 1, wherein the macular degeneration is dry macular degeneration caused by epithelial-mesenchymal transition.

5. The method of claim 1, wherein the pharmaceutical composition further comprises a pharmaceutically acceptable diluent or carrier.

* * * * *